US012035093B2

United States Patent
Trotter et al.

(10) Patent No.: US 12,035,093 B2
(45) Date of Patent: Jul. 9, 2024

(54) EARPIECE FITTING SYSTEM

(71) Applicant: Bose Corporation, Framingham, MA (US)

(72) Inventors: John Andrew Trotter, Sudbury, MA (US); Kemal Kulovic, Arlington, MA (US); John Benton, Northbridge, MA (US)

(73) Assignee: Bose Corporation, Framingham, MA (US)

( * ) Notice: Subject to any disclaimer, the term of this patent is extended or adjusted under 35 U.S.C. 154(b) by 195 days.

(21) Appl. No.: 17/692,019

(22) Filed: Mar. 10, 2022

(65) Prior Publication Data
US 2022/0201379 A1 Jun. 23, 2022

Related U.S. Application Data

(63) Continuation of application No. PCT/US2020/049860, filed on Sep. 9, 2020.

(60) Provisional application No. 62/898,403, filed on Sep. 10, 2019.

(51) Int. Cl.
H04R 1/10 (2006.01)

(52) U.S. Cl.
CPC ......... H04R 1/1016 (2013.01); H04R 1/1041 (2013.01); H04R 1/105 (2013.01); H04R 1/1066 (2013.01)

(58) Field of Classification Search
CPC .... H04R 1/1016; H04R 25/65; H04R 25/652; H04R 25/656; H04R 2460/09; H04R 2460/11; H04R 2460/15; A61F 11/10
See application file for complete search history.

(56) References Cited

U.S. PATENT DOCUMENTS

| 8,965,518 | B1 | 2/2015 | Ellrich et al. | |
|---|---|---|---|---|
| 9,168,171 | B2 | 10/2015 | Rogers | |
| 2004/0002665 | A1* | 1/2004 | Parihar | A43B 7/146 |
| | | | | 600/587 |
| 2010/0300897 | A1* | 12/2010 | Savage | A61B 5/6846 |
| | | | | 204/403.01 |
| 2013/0136285 | A1* | 5/2013 | Naumann | H04R 25/656 |
| | | | | 381/329 |
| 2015/0360030 | A1* | 12/2015 | Cartledge | A61N 1/3603 |
| | | | | 607/136 |
| 2018/0193641 | A1* | 7/2018 | Black | A61N 1/36028 |

(Continued)

FOREIGN PATENT DOCUMENTS

| WO | 2015/192114 A1 | 12/2015 |
|---|---|---|
| WO | 2018/071630 A1 | 4/2018 |

OTHER PUBLICATIONS

International Search Report and The Written Opinion of the International Searching Authority dated Nov. 19, 2020 for PCT Application No. PCT/US2020/049860.

Primary Examiner — Mark Fischer
(74) Attorney, Agent, or Firm — Hoffman Warnick LLC

(57) ABSTRACT

A fitting system for an earpiece that comprises a support structure that is configured to contact at least one of the ear canal or the concha of an ear of a user, including at least first and second spaced electrodes that are each configured to contact the user's skin, circuitry that is configured to determine an impedance between the first and second electrodes, and a controller, responsive to the determined impedance, for causing the earpiece support structure to move.

19 Claims, 5 Drawing Sheets

(56) References Cited

U.S. PATENT DOCUMENTS

2018/0235540 A1  8/2018  Kirszenblat et al.
2020/0037061 A1* 1/2020  Boulanger ........... H04R 1/1041

* cited by examiner

EARPIECE FITTING SYSTEM

CROSS-REFERENCE TO RELATED APPLICATIONS

This application claims priority of PCT/US2020/049860 filed on Sep. 9, 2020, which itself claimed priority of Provisional Application 62/898,403 filed on Sep. 10, 2019.

BACKGROUND

This disclosure relates to a system for fitting an earpiece on a user.

Earpieces can be used to send and/or receive electrical signals to/from the body, and/or to deliver sound to the ear. Some earpieces engage with one or both of the ear canal and the concha. A tight fit to the ear canal/concha helps the earpiece to stay in place as the head is moved and helps to maintain the sound quality. Also, when earpieces are used to sense and/or deliver electrical signals from or to the body (e.g., when they are used for vagus nerve stimulation (VNS) or to sense heart rhythm), the electrodes need to make good contact with the skin.

SUMMARY

All examples and features mentioned below can be combined in any technically possible way.

In one aspect, a fitting system for an earpiece that comprises a support structure that is configured to contact at least one of the ear canal or the concha of an ear of a user includes first and second spaced electrodes that are each configured to contact the user's skin, circuitry that is configured to determine an impedance between the first and second electrodes, and a controller, responsive to the determined impedance, for causing the earpiece support structure to move. When there are three or more electrodes, the impedance may be determined between each pair of electrodes.

Examples may include one of the above and/or below features, or any combination thereof. The earpiece support structure may comprise shape memory material that is configured to change shape upon the application of a stimulus. The shape memory material may be electrically conductive, in which case the stimulus can be resistive heating. The stimulus may be heat, may be electrical, or may be light-based. The controller may be configured to control an application of electrical current to the shape memory material, to cause heating of the shape memory material.

Examples may include one of the above and/or below features, or any combination thereof. The earpiece support structure may be configured to be located in the ear canal. At least one of the electrodes may be carried by the earpiece support structure and configured to be located in the ear canal. The earpiece support structure may be configured to expand. The earpiece support structure expansion may be radial.

Examples may include one of the above and/or below features, or any combination thereof. The controller may be configured to cause an extent of motion of the earpiece support structure that is directly related to the determined impedance. The controller may be configured to cause motion of the earpiece support structure until the impedance drops below a threshold impedance level.

Examples may include one of the above and/or below features, or any combination thereof. The earpiece support structure may comprise an expansion mechanism. The earpiece support structure may comprise a fluidly-driven expansion system. The electrodes may comprise a hydrogel. The earpiece support structure may comprise a headband that is configured to push eartips into contact with the ear.

Examples may include one of the above and/or below features, or any combination thereof. The controller may be further configured to apply a vagus nerve stimulation electrical signal to at least one of the ear canal or concha. The first electrode may be configured to be in contact with at least one of the ear canal or the concha. The vagus nerve stimulation electrical signal may be applied between the first and second electrodes.

DETAILED DESCRIPTION

Figure 1:
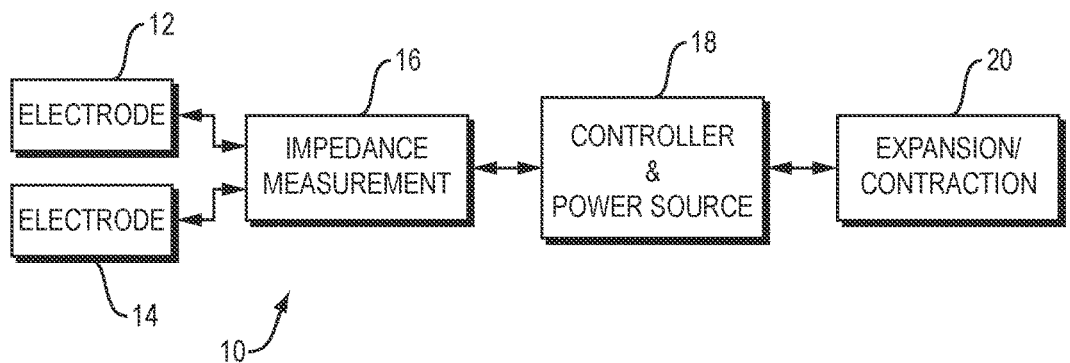
FIG. 1 is schematic block diagram of an earpiece fitting system.

This disclosure describes an earpiece. An earpiece is part of a device that is placed against or proximate, or inserted into, the opening of the ear canal. The figures and descriptions following in some cases show a single earpiece device. There may be a single stand-alone earpiece or there may be a pair of earpieces, one for each ear. The earpiece may be connected mechanically to another earpiece, for example by a headband and/or by leads that conduct signals to the earpiece. The earpiece may include components for wirelessly receiving signals. An earpiece may include components of an active noise reduction (ANR) system. Earpieces may also include other functionality, such as the ability to receive or send electrical signals from or to the body.

In an in the ear, around the ear, or on the ear earpiece, there may be a headband or other support structure. There may also be at least one housing or other structure that is arranged to sit in or on or over or proximate an ear of the user. The headband can be collapsible or foldable, and can be made of multiple parts. Some headbands include a slider, which may be positioned internal to the headband, that provides for any desired translation of the housing.

Some earpieces (including but not limited to earbuds) engage with one or both of the ear canal and the concha. A tight fit to the ear canal/concha helps the earbud to stay in place as the head is moved, and helps to maintain the sound quality. Also, when earpieces are used to sense and/or deliver electrical signals from or to the body (e.g., when they are used for vagus nerve stimulation or to sense heart rhythm), the electrodes need to make good contact with the skin.

The present earpiece fitting system can, in one non-limiting example, include a support structure that is configured to contact the ear canal and/or the concha. Fitting of the earpiece can be accomplished by causing the support structure to move. The movement can be such that the support structure is held closer to or more tightly to the skin. The movement helps ensure good contact with the skin. Good contact can help with electrical signal delivery and reception, and with audio quality when the earpiece is part of a headphone.

In some non-limiting examples the fit is based at least in part on a measurement of the impedance between two or more electrodes that are both in electrical contact with the skin. At least one electrode can be configured to contact the skin in the ear canal and/or the concha. A second electrode can be configured to contact the skin in or close to the ear (e.g., also in one or both of the ear canal and the concha, or behind or in front of the ear). If there are more than two electrodes, the impedance can be measured between every pair of the electrodes. The movement of the support structure can be based on the impedance. In some non-limiting examples the movement continues until the impedance reaches at or below an acceptable threshold level. The total amount of movement can be directly related to the impedance—if the impedance is high there is more movement as compared to the extent of movement when the impedance is lower.

In some non-limiting examples the movement can be accomplished by including shape memory material in the support structure. The shape memory material will change shape upon application of a stimulus such as an electrical stimulus, a light-based stimulus, or a heat-based stimulus. Non-limiting examples of the shape memory material include a shape memory alloy, or a shape memory polymer. A shape memory alloy typically changes shape when heated above a critical point. The alloy can be electrically conductive, and the heating can take place via resistive heating. A controller can be used to control the application of electrical power to the shape memory alloy, to cause resistive heating and thus case motion of the support structure.

The support structure can be configured such that the movement accomplishes a tighter fit of the support structure to the body (e.g., the ear canal or the concha). The efficacy of the fit can be determined based on the impedance measurements. When the impedance is low enough, the electrodes will be useful to send and receive electrical signals, as described above. Also, low impedance can be indicative of a good acoustic seal (e.g., a good seal of an ear tip of an earbud to the ear canal). A good acoustic seal to the ear canal can help the earpiece to deliver better sound quality to the user. Or it can ensure good conductivity for delivery or sensing of electrical signals, such as with VNS.

FIG. 1 is schematic block diagram of an earpiece fitting system 10. Earpiece fitting system 10 comprises electrodes 12 and 14. These electrodes are configured to be in contact with the user's skin when the earpiece is worn on the body. The electrodes can be used as part of an impedance measurement system. The electrodes (or a second pair of electrodes, not shown in FIG. 1) can also be used to receive and/or deliver electrical signals from and/or to the body, as described elsewhere herein. Impedance measurement circuitry 16 is responsive to electrodes 12 and 14 and is configured to determine an impedance between the electrodes. The impedance measurement can be used as an indication of the intimacy of the contact of the electrodes with the skin. Note that system 10 can include two or more electrodes. When there are more than two electrodes, impedance measurements can be taken between different pairs of electrodes, as is further described below.

Controller and power source module 18 can, in response to the impedance, cause expansion/contraction system 20 to move the earpiece support structure. For example, if the impedance is high (indicative of too loose a fit), module 18 can cause system 20 to move the earpiece support structure in a way that results in better contact of the electrodes with the skin and thus a reduced impedance. In one example the motion continues until the impedance reaches or goes below a predetermined threshold level, indicative of acceptable contact of the electrodes with the skin. In some cases, if the impedance is too low this might be considered indicative of a fit that is so tight that it might be uncomfortable; in this case controller and power source 18 may enable system 20 to move the earpiece support structure slightly away from the skin until the impedance reaches a more reasonable level.

In cases where movement of the earpiece support structure is facilitated with a shape memory material, the shape memory material can change shape when it is heated. Alternatively, shape memory materials can change shape when exposed to an electrical stimulus, or a light-based stimulus. In some cases the shape memory material will return to its original shape when it is cooled. In cases where the shape memory material is electrically conductive (as with a shape memory alloy), heating can occur via resistive heating; in this case controller and power source 18 is enabled to provide electrical current to the shape memory alloy that is part of system 20. The shape memory alloy can be configured such that its shape change due to heating causes the earpiece support structure to push more tightly against the skin. When the heat source is removed (e.g., by lowering or stopping the current) the shape memory alloy will return to its original shape, thereby pulling the earpiece support structure away from the skin.

Figure 2A:
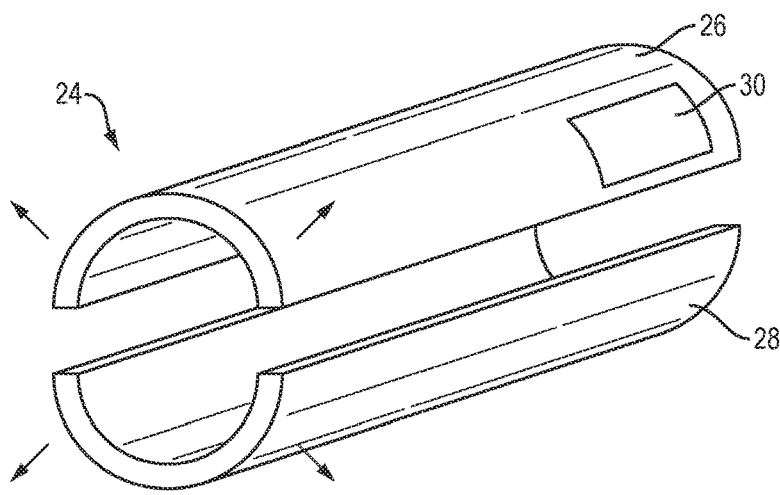
FIG. 2A is a partial view of an earpiece that is configured to be fitted to a user's ear, illustrating expanding members of the earpiece.

FIG. 2A is a partial view of an earpiece that is configured to be fitted to a user's ear, illustrating expanding members of the earpiece. Generally semi-circular members 26 and 28 are arranged opposing one another as shown, to form a generally cylindrical structure 24. Members 26 and 28 can be made from or include shape memory material (e.g., a shape memory alloy or a shape memory polymer). When a stimulus that causes a shape change of the shape change material is applied to members 26 and/or member 28, the member expands radially outwardly, in the direction of the arrows. Expansion of one or both of members 26 and 28 causes the diameter of structure 24 to increase. If structure 24 is part of an earpiece support structure (not shown) that is configured to be located in the ear canal, such expansion will cause a tighter fit of the earpiece support structure in the ear. Likewise, if the stimulus is removed from member 26 and/or member 28, the earpiece support structure will contract and the fit in the ear canal will be looser.

As described relative to FIG. 1, the earpiece fitting system includes electrodes that can be used for impedance measurement and/or to receive and/or deliver electrical signals from and/or to the body. One such electrode 30 is depicted in FIG. 2A, in which it is carried by member 26. The second electrode would be in a different location on the earpiece and that is configured to contact the skin when the earpiece is in use. In one non-limiting example the second electrode could be carried by member 28.

Figure 2B:
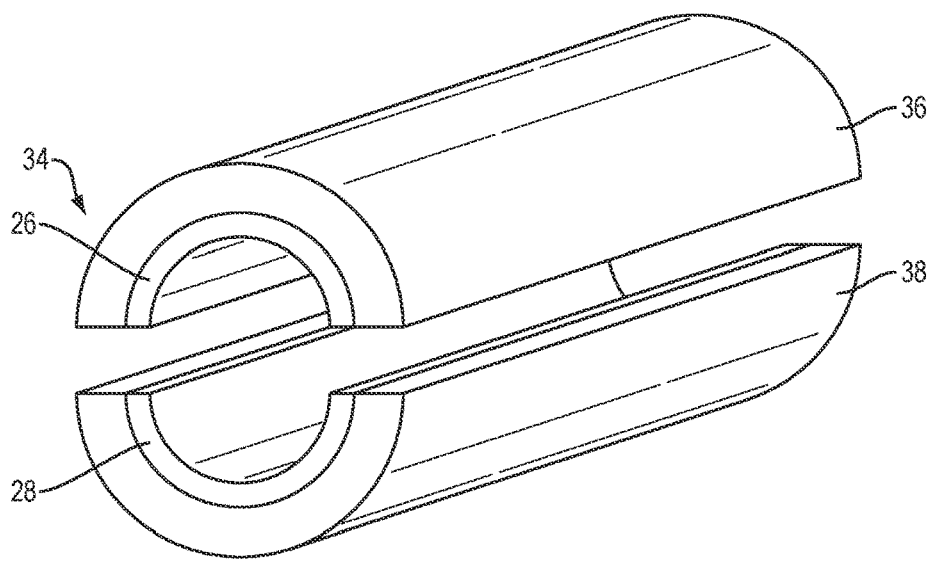
FIG. 2B illustrates the expanding members and electrodes of the earpiece of FIG. 2A.

FIG. 2B illustrates the expanding members 26 and 28, and two electrodes 36 and 38 that can be used with the earpiece that is partially illustrated in FIG. 2A. Electrodes 36 and 38 can be carried on the outside of members 26 and 28, respectively. Electrodes 36 and 38 are configured to contact the ear canal when the earpiece is used. Electrodes 36 and 38 can be made from or comprise a soft conductive material so that they are able to conform better to the contours of the user's ear canal while still being able to send/receive electrical signals. In one non-limiting example electrodes 36 and 38 are made from a conductive hydrogel. Hydrogels are known in the art, so are not further described herein. A hydrogel can be sufficiently conductive to act as an electrode and can be sufficiently soft and flexible to conform to an ear canal.

Figure 3:
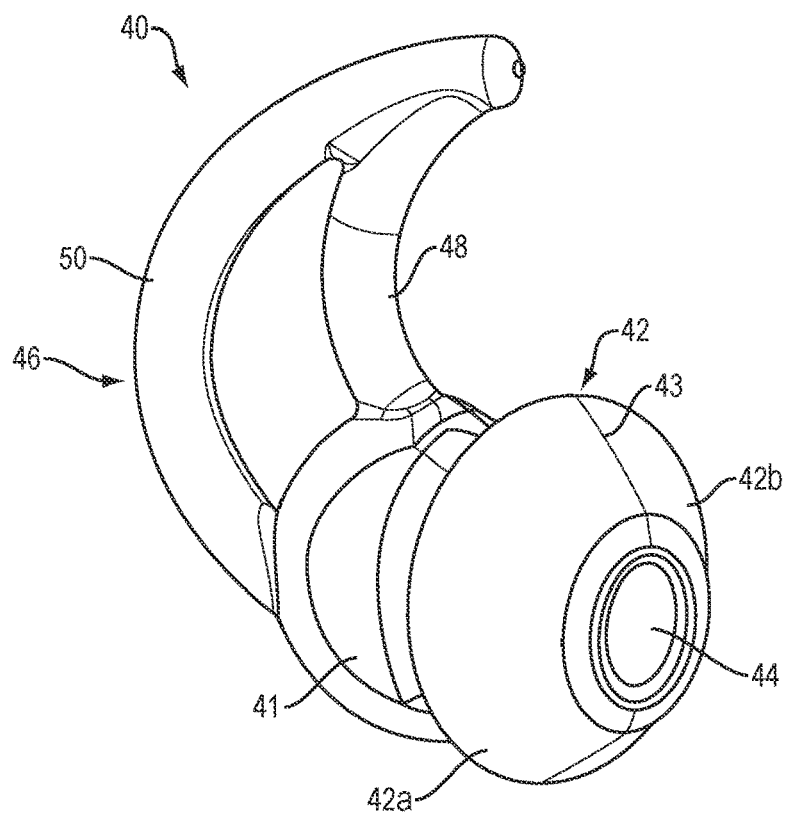
FIG. 3 illustrates an earpiece.

FIG. 3 illustrates a earpiece that comprises the subject fitting system. Earpiece 40 includes a conical ear tip 42 that is configured to be pushed into the ear canal (not shown). Ear tip 42 can be made from a soft biocompatible material such as a silicone. The conical shape helps to seat the ear tip in the ear canal and the softness helps to create a good acoustic seal, to help keep environmental sounds out of the ear canal. The electrodes may (but need not be) carried on ear tip 42. In one non-limiting example ear tip 42 is divided into two electrically separate portions 42a and 42b, divided by junction or separator 43. Some or all of the outside of portions 42a and 42b can be made electrically conductive (e.g., with a conductive coating or by constructing the ear tip of a conductive material), so that the portions can act as electrodes. Body 41 carries the earpiece electronics and power source, and an electro-acoustic transducer that is configured to deliver sound out of opening 44. Tail 46 comprising spaced portions 48 and 50 is configured to seat in the concha and helps hold the earpiece in the ear as the user moves. Earpieces with the configuration shown in FIG. 3 are illustrative but not limiting of this disclosure. Such earpieces are further disclosed in U.S. Patent Application Publication 2018/0235540, the entire disclosure of which is incorporated herein by reference for all purposes.

Figure 4:
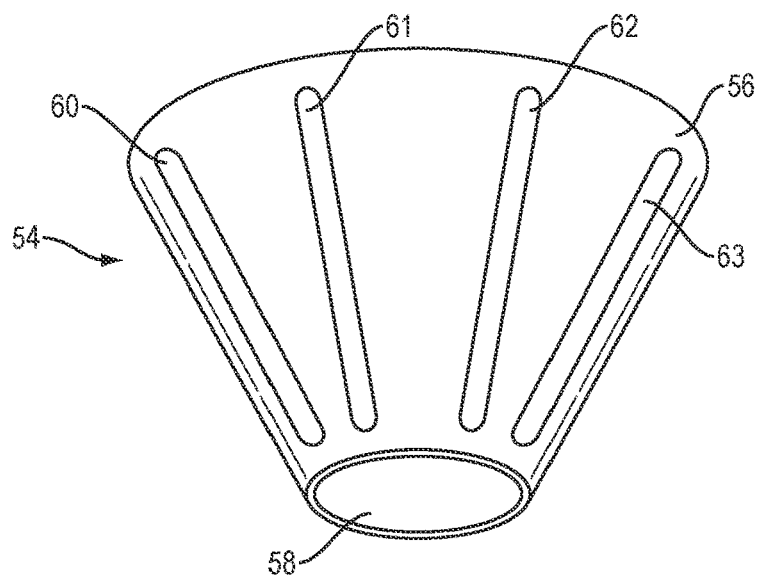
FIG. 4 illustrates an expanding ear tip for an earpiece.

FIG. 4 illustrates an expanding ear tip 54 for an earpiece. Ear tip 54 is conically-shaped, like ear tip 42, FIG. 3, and includes distal opening 58 for sound delivery into the ear canal. FIG. 4 illustrates one non-limiting manner by which a conical ear tip can be made expandable radially, to alter the tightness of the fit in the ear canal. Expansion can be enabled with one or more portions 60-63 of shape memory material that are in or on the ear tip portion 56. When heat (e.g., such as by resistive heating with electrical current) or another stimulant that causes shape change (such as an electrical or a light-based stimulant) is supplied to any one or more of portions 60-63 the portion will change shape. If the shape change is designed to push the ear tip outwardly, into the wall of the ear canal, the shape change can alter the fit and tightness of the ear tip in the ear canal. Also, by using a plurality of separate portions of shape change material that are separately heated or cooled, shape change of the ear tip can be tailored. For example, if only part of the support structure needs to be expanded or moved, the portion of the shape change material that is configured to expand or move this part of the support structure can be heated. Expansion of ear tip portion 56 can be accomplished in a desired manner. Non-limiting examples of expansion techniques include an inflatable bladder (not shown) inside portion 56 that is enabled to push out radially, or a mechanism that is able to draw one cone into another cone, or by the use of an elastic cone that is held closed by a band where tension on the band can be released (e.g., via use of a wire made of shape memory material).

Figure 5:
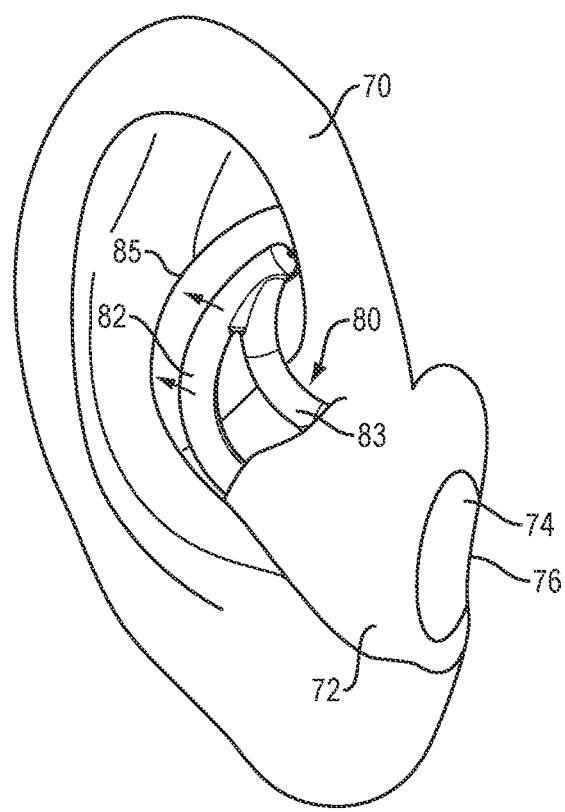
FIG. 5 is a partial view of a movable tail portion of an earpiece.

FIG. 5 is a partial view of a movable tail portion of an earpiece, where the tail portion motion helps to hold the earpiece in the ear and can also help to ensure a sufficient conductive contact of the electrodes with the skin of the ear. For example, one or both electrodes (not shown in this drawing) could be on or in one or both of portions 82 and 83 of tail 80. Tail 80 could be configured like tail 46, FIG. 3. In this non-limiting example, tail portion 82 comprises shape memory material (not shown) that when heated or otherwise stimulated can cause portion 82 to move in the direction of the arrows, such that it is closer to or is pushed more tightly against ear portion 85 that borders concha 72. Ear 70 also includes tragus 76 and ear canal opening 74.

Figure 6:
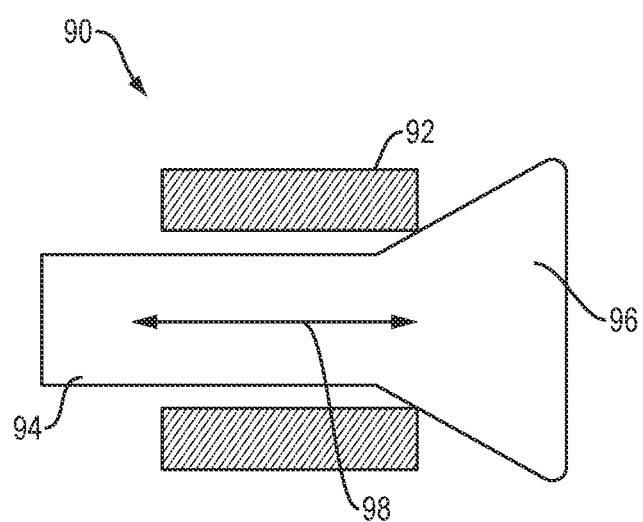
FIG. 6 is a partial cross-sectional view of an earpiece support structure expansion mechanism.
Figure 7:
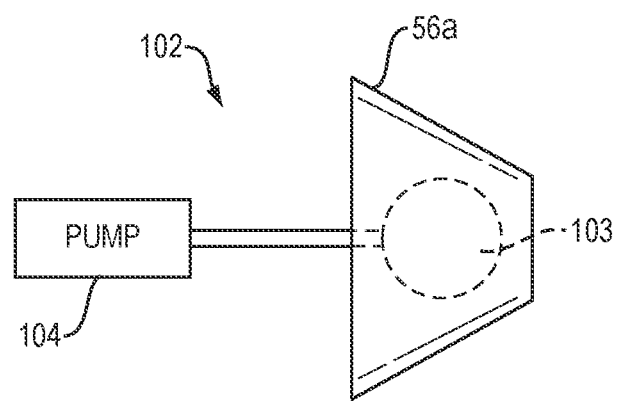
FIG. 7 illustrates a fluidly-driven earpiece support structure expansion mechanism.

The desired movement (e.g., expansion) of the earpiece support structure can be accomplished in any desired manner. Non-limiting examples of potential motion-causing technologies that could be used include any one or more of: shape memory materials, mechanical devices, electromechanical devices, and fluidically-activated devices. FIG. 6 is a partial cross-sectional view of a mechanical earpiece support structure expansion mechanism 90. Mechanism 90 is like an expanding anchor, with outer sleeve 92 that can be radially expanded and contracted by driving wedge 96 in the direction of arrow 98, in and out of the sleeve interior. Wedge 96 can be part of a driven structure 94 (e.g., a screw mechanism). FIG. 7 is a simplified view of a fluidically-activated earpiece support structure motion (e.g., expansion) system 102. System 102 can include a fluid-filled expandable bladder 103 that can be expanded by increasing the pressure of the fluid. The pressure of the fluid (e.g., a gas such as air, or a liquid such as water) can be varied by controlling operation of fluid pump 104 that is fluidly coupled to bladder 103. If bladder 103 is located inside of a flexible ear tip portion 56a then the bladder can be used to tighten or loosen the fit of the ear tip portion. Another alternative manner of contracting and expanding a conical ear tip portion would be a loop of shape memory material (e.g., muscle wire) coupled to the inside of the cone, where the wire is configured to contract or expand in order to contract or expand the cone.

Figure 8:
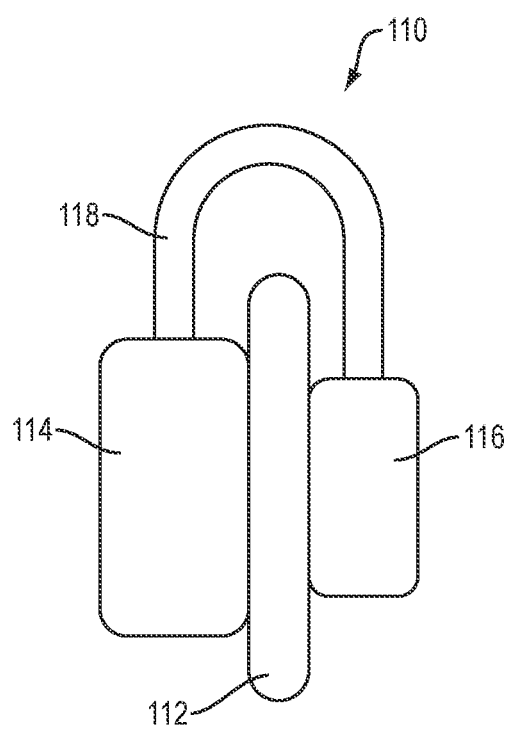
FIG. 8 illustrates an earpiece mounted on a head.

FIG. 8 schematically illustrates a earpiece mounted on a head. Earpiece 110 comprises earpiece support structure 116 that is configured to be located close to, on, or in ear 112. Structure 116 may or may not include an electro-acoustic transducer. Earpiece 110 further comprises portion 114 that is located on the head proximate the ear and/or against the outside of ear 112. Portion 118 connects portions 114 and 116. Earpiece 110 is configured such that one or both of portions 114 and 116 can be moved closer together, to thereby tighten the fit on the ear in a clamping-type motion. This movement can be accomplished using a shape change material that is enabled to pull portions 114 and 116 closer together or farther apart, to thereby cause or release clamping pressure.

Figure 9:
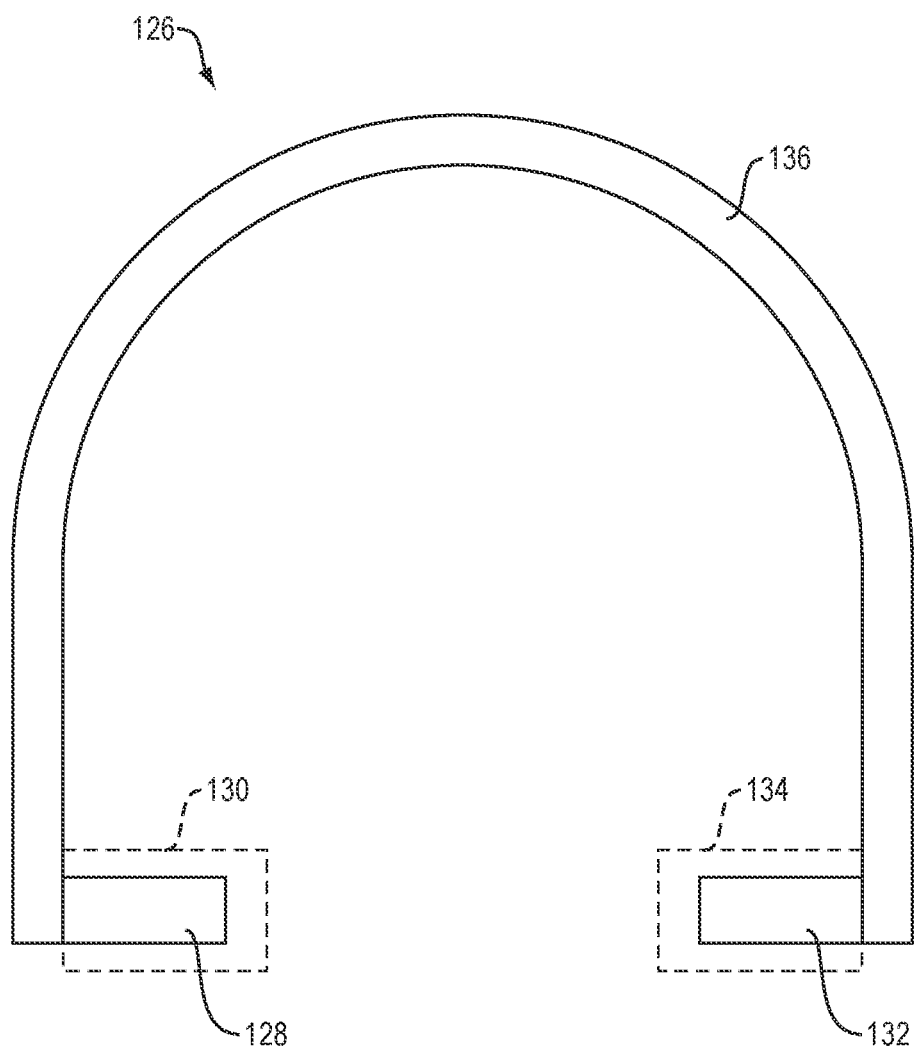
FIG. 9 illustrates an earpiece fitting system.

FIG. 9 illustrates a earpiece fitting system for fitting ear tips 128 and 132 into ear canals 130 and 134. In this example a headband or connecting band 136 mechanically couples ear tips 128 and 132. Band 136 may be considered part of the earpiece support structure. Band 136 can be configured to move ear tips 128 and 132 in and out of and/or radially outwardly or inwardly of ear canals 130 and 134. One manner in which such motion can be accomplished is with a vibrating device (like a cell phone vibrator) carried by band 136 such that when activated it is effective to cause vibration of an ear tip. This vibration is like a scrubbing action of the ear tip in the ear canal that can help to better seat the ear tip in the ear canal. Inward and outward motion of ear tips 128 and 132 can be accomplished with shape memory material that is configured compress or relax band 136 to move the ear tips into and out of the ear canal, to accomplish a desired fit. Inward and outward movement can also be achieved by tightening or loosening the band 136 with a mechanical spring and motor, muscle wire (e.g., wire made of shape memory material), or other device.

The earpiece fitting system can also be used for earpieces that are used to send and/or receive electrical signals to/from the body, using electrodes that are in contact with the skin. One non-limiting example is vagus nerve stimulation. Vagus nerve stimulation involves applying controlled electrical signals to the skin in the ear canal and/or the concha. Typically but not necessarily the earpiece would comprise one electrode that is configured to be in electrical contact with the skin in the ear canal and/or the concha. A second electrode that is needed to complete the vagus nerve stimulation circuit can be in electrical contact with the skin in the ear canal and/or the concha, or another location on or close to the ear (e.g., against the back of the ear just behind the concha) or locations on or in or proximate the other ear. System 10, FIG. 1, can be used for vagus nerve stimulation. One or both of electrodes 12 and 14 can be used for vagus nerve stimulation. Alternatively, there can be one or more additional electrodes (not shown in FIG. 1) that are used for the vagus nerve stimulation.

In one non-limiting example the same electrodes are used for both impedance sensing and vagus nerve stimulation. For example, soft conductive electrodes such as electrodes 36 and 38 can be used. The expansion system can be used to adjust the fit of the electrodes in the ear canal and/or the concha. When the fit is sufficient to allow the system to be used for vagus nerve stimulation, the impedance measurement system can be disabled and a vagus nerve stimulation system can be enabled. The vagus nerve stimulation system can used controller and power source 18 that provides appropriate vagus nerve stimulation electrical signals (as is known in the art) to electrodes 36 and 38. In non-limiting examples the impedance measurement system can be periodically enabled to make sure the earpiece fit is still appropriate, and it can also be enabled to adjust the fit as necessary as described elsewhere herein. Also, since the vagus nerve stimulation system is applying current to the electrodes that are also used for impedance measurement, changes in impedance can also be detected by monitoring changes in the vagus nerve stimulation electrical signals. For example, if the contact of the electrodes to the skin becomes compromised, the impedance will increase which will cause a decrease in current flow (presuming a constant voltage). Module 18, FIG. 1, can detect such changes in current flow and readjust the fit using expansion/contraction system 20.

Elements of FIG. 1 are shown and described as discrete elements in a block diagram. These may be implemented as one or more of analog circuitry or digital circuitry. Alternatively, or additionally, they may be implemented with one or more microprocessors executing software instructions. The software instructions can include digital signal processing instructions. Operations may be performed by analog circuitry or by a microprocessor executing software that performs the equivalent of the analog operation. Signal lines may be implemented as discrete analog or digital signal lines, as a discrete digital signal line with appropriate signal processing that is able to process separate signals, and/or as elements of a wireless communication system.

When processes are represented or implied in the block diagram, the steps may be performed by one element or a plurality of elements. The steps may be performed together or at different times. The elements that perform the activities may be physically the same or proximate one another, or may be physically separate. One element may perform the actions of more than one block. Audio signals may be encoded or not, and may be transmitted in either digital or analog form. Conventional audio signal processing equipment and operations are in some cases omitted from the drawing.

Examples of the systems and methods described herein comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the disclosure.

A number of implementations have been described. Nevertheless, it will be understood that additional modifications may be made without departing from the scope of the inventive concepts described herein, and, accordingly, other examples are within the scope of the following claims.

What is claimed is:

1. A fitting system for an earpiece that comprises a support structure that is configured to contact at least one of the ear canal or the concha of an ear of a user, wherein the earpiece support structure comprises shape memory material that is configured to change shape upon the application of a stimulus, to expand the earpiece support structure, the earpiece fitting system comprising:
   at least first and second spaced electrodes that are each configured to contact the user's skin;
   circuitry that is configured to determine an impedance between the first and second electrodes; and
   a controller, responsive to the determined impedance, for causing the application to the shape memory material of the stimulus that causes the earpiece support structure to expand such that it fits more tightly in the ear canal or concha, wherein the expansion results in a reduced impedance between the first and second electrodes that is indicative of a better fit of the earpiece.

2. The earpiece fitting system of claim 1, wherein the shape memory material is electrically conductive, and wherein the stimulus comprises resistive heating.

3. The earpiece fitting system of claim 2, wherein the controller is configured to control an application of electrical current to the shape memory material, to cause heating of the shape memory material.

4. The earpiece fitting system of claim 1, wherein the stimulus comprises heat, an electrical stimulus, or a light-based stimulus.

5. The earpiece fitting system of claim 1, wherein the earpiece support structure is configured to be located in the ear canal.

6. The earpiece fitting system of claim 5, wherein at least one of the electrodes is carried by the earpiece support structure and is configured to be located in the ear canal.

7. The earpiece fitting system of claim 1, wherein the earpiece support structure expansion is radial.

8. The earpiece fitting system of claim 1, wherein the controller is configured to cause an extent of expansion of the earpiece support structure that is directly related to the determined impedance.

9. The earpiece fitting system of claim 1, wherein the controller is configured to cause expansion of the earpiece support structure until the impedance drops below a threshold impedance level.

10. The earpiece fitting system of claim 1, wherein the earpiece support structure comprises an expansion mechanism.

11. The earpiece fitting system of claim 1, wherein the earpiece support structure comprises a fluidly-driven expansion system.

12. The earpiece fitting system of claim 1, wherein the electrodes comprise a hydrogel.

13. The earpiece fitting system of claim 1, wherein the earpiece support structure comprises a headband that is configured to push eartips into contact with the ear.

14. The earpiece fitting system of claim 1, wherein the controller is further configured to apply a vagus nerve stimulation electrical signal to at least one of the ear canal or concha.

15. The earpiece fitting system of claim 14, wherein the first electrode is configured to be in contact with at least one of the ear canal or the concha.

16. The earpiece fitting system of claim 14, wherein the vagus nerve stimulation electrical signal is applied between the first and second electrodes.

17. The earpiece fitting system of claim 1, comprising more than two electrodes, and wherein the circuitry is configured to determine the impedance between each pair of electrodes.

18. A fitting system for an earpiece that comprises a support structure that is configured to contact at least one of the ear canal or the concha of an ear of a user, the earpiece fitting system comprising:
at least first and second spaced electrodes that are each configured to contact the user's skin;
circuitry that is configured to determine an impedance between the first and second electrodes; and
a controller, responsive to the determined impedance, for causing the earpiece support structure to move wherein the controller is configured to cause motion of the earpiece support structure until the impedance drops below a threshold impedance level.

19. A fitting system for an earpiece that comprises a support structure that is configured to contact at least one of the ear canal or the concha of an ear of a user, the earpiece fitting system comprising:
at least three spaced electrodes that are each configured to contact the user's skin;
circuitry that is configured to determine an impedance between each pair of electrodes; and
a controller, responsive to the determined impedances, for causing the earpiece support structure to move.

* * * * *